United States Patent [19]

Blobel et al.

[11] 4,312,942

[45] Jan. 26, 1982

[54] PROCESS FOR THE EXTRACTION OF MICROORGANISMS AND DIAGNOSTIC AGENTS CONTAINING THEM

[75] Inventors: Hans-Georg Blobel, Leihgestern; Werner Schaeg, Giessen; Jörg Brückler, Heuchelheim, all of Fed. Rep. of Germany

[73] Assignee: Behringwerke Aktiengesellschaft, Marburg, Fed. Rep. of Germany

[21] Appl. No.: 839,846

[22] Filed: Oct. 6, 1977

Related U.S. Application Data

[63] Continuation of Ser. No. 837,816, Sep. 29, 1977, abandoned.

[30] Foreign Application Priority Data

Oct. 2, 1976 [DE] Fed. Rep. of Germany ....... 2644622

[51] Int. Cl.$^3$ .......................... C12Q 1/56; C12R 1/08; C12N 1/20
[52] U.S. Cl. .......................................... 435/7; 435/13; 435/253; 23/230 B; 424/12
[58] Field of Search ................... 195/99, 100, 101, 59, 195/75, 96; 23/230 B; 424/8, 12, 85, 87; 435/68, 713, 883, 863, 243, 245, 253, 170; 260/112 R, 112 B

[56] References Cited

U.S. PATENT DOCUMENTS

| | | | |
|---|---|---|---|
| 3,936,354 | 2/1976 | La Pointe et al. | 195/100 |
| 3,966,898 | 6/1976 | Sjöquist et al. | 195/103.5 A |
| 3,990,947 | 11/1976 | Butler et al. | 195/99 |
| 4,035,238 | 7/1977 | Meyer et al. | 195/100 |
| 4,245,039 | 1/1981 | Heimburger et al. | 435/13 |

FOREIGN PATENT DOCUMENTS

2644622 4/1978 Fed. Rep. of Germany .......... 435/7

OTHER PUBLICATIONS

Kabat et al. *Experimental Immunochemistry*, Charles C. Thomas, Springfield (1948), pp. 260-263.

*Primary Examiner*—Thomas Wiseman
*Attorney, Agent, or Firm*—Curtis, Morris & Safford

[57] ABSTRACT

There is provided a process for extraction of a microorganism, which comprises treating said microorganism with a 4 to 8 molar aqueous solution of a guanidine salt, subsequently washing it to liberate it from the salt and thus obtaining it and diagnostic agents containing a microorganism so extracted.

15 Claims, No Drawings

PROCESS FOR THE EXTRACTION OF MICROORGANISMS AND DIAGNOSTIC AGENTS CONTAINING THEM

This application is a continuation in part of application Ser. No. 837,816 filed Sept. 29, 1977 and now abandoned.

The present invention relates to a process for the extraction of microorganisms, especially staphylococci, and diagnostic agents containing extracted microorganisms, which agents may be used for example for the detection of fibrinogen or fibrin fission products of for binding immune globulin or the $F_c$ fragment thereof, and thus for determining an antigen.

As is known, microorganisms contain a great number of substances which cause various reactions. Due to the fact that such reactions often overlap, individual mechanisms can be seldom observed. However, the observation of differentiated reactions caused by individual sections of the microorganisms is often required, so that the remaining undesirable portions have to be eliminated.

It is known that a number of *Staphylococcus aureus* strains react with fibrinogen and with the degradation products of fibrin, showing a clumping effect. The factor responsible for the reaction is known as Clumping Factor (CF). Because of the simple operation mode, this Clumping Factor reaction has become important in the practice for the diagnosis of increased fibrinolysis. For carrying out the Clumping Factor reaction, selected CF-positive staphylococci only have been hitherto used. It is especially undesirable that the corresponding staphylococci form soluble coagulase besides CF. Moreover, a number of *Staphylococcus aureus* strains have the undesirable property of spontaneous agglutination which is supposed to be due to certain non characterized proteins.

So, there is a demand for staphylococci which contain Clumping Factor but not soluble coagulase and which do not tend to spontaneous agglutination.

It is furthermore known that certain microorganisms contain a polypeptide which is capable of binding the so-called $F_c$ part of antibody molecules. In the case of staphylococci, this polypeptide is called protein A. In order to suppress troublesome side reactions, $F_c$-binding microorganisms are worked up to obtain the polypeptide, which is generally linked to a solid carrier.

So, there is a demand for polypeptide linked to a carrier for binding the $F_c$ part of antibody molecules, which allows a trouble-free determination of antigens.

In accordance with this invention, both these objects are achieved by subjecting microorganisms, especially staphylococci, to a special extraction process.

Subject of the present invention is therefore an extraction process for eliminating undesirable portions of a microorganism usable as reagent, preferably *Staphylococcus aureus*, which comprises treating the microorganism with a 4 to 8 molar, preferably 6 molar, aqueous solution of a guanidine salt, subsequently liberating it from the salt and thus obtaining it. Optionally, it may then be lyophilized.

In preferred embodiments, and with a view toward their use, either Clumping Factor-positive microorganisms, especially Clumping Factor-positive staphylococci, or $F_c$ part-binding peptide containing microorganisms, especially protein A containing staphylococci, are used.

For use as CF reagent, the staphylococci are advantageously suspended in a buffer solution, optionally containing a suspension stabilizer. Suitable buffer solutions are the buffer systems usual for biochemical operations, for example tris-hydroxymethyl-aminomethane hydrochloride, imidazole/sodium chloride buffer or phosphate buffered saline solution. In the case where suspension stabilizers are desirable, it is recommended to employ proteins of the albuminoid type, for example serum albumin, preferably bovine serum albumin; the concentration thereof being from 0.005 to 0.1%, preferably 0.01%.

The germ concentration of the staphylococci in the corresponding buffer solution preferably adjusted to a pH around the neutral point, for example from 7.0 to 7.5, is about 0.1 to 10%. Especially advantageous is a concentration of about 0.15 to 0.3%.

Suitable suspension stabilizers and stabilizers for maintaining the activity of the lyophilized product are above all polyols, the concentration of which in the aqueous buffer solution used for the suspension of the staphylococci and having a pH of preferably 7.0 to 7.7 is from 3 to 50 percent. The suitable polyols are in a molecular weight range of from 62 to 500,000. Examples are the following substances: glycerin, glucose, mannitol, polyethyleneglycol, dextran or Ficoll, of which those having a molecular weight of from 70,000 to 400,000 are especially suitable. While it is particularly advantageous to add 50 percent of glycerin to the suspension, 3 percent of mannitol, polyethyleneglycol, dextran or Ficoll are already sufficient for achieving an excellent stability of the suspension and storage stability of the extracted staphylococci.

Titration is the most suitable determination method, and especially favorable is a micro-titration method where about 50 $\mu$l of a gradually increased dilution series of the solution to be determined, for example blood plasma or blood serum, especially human plasma or human serum, are added to about 20 $\mu$l of the buffered germ suspension of about 0.15 to 0.3%.

In the subsequent incubation of the mixture, there has been found surprisingly that the sensitivity with respect to the detection of fibrin fission products can be considerably increased by intensely shaking the reaction mixtures. Limitation of the period of shaking until taking the reading of the reaction being complete is recommended. A period of from 3 to 10 minutes is adhered to in the micro-titration process.

In a further embodiment of the invention, there has been found that the clumping reaction of the microorganisms, preferably staphylococci, is especially well readable when they are dyed with a suitable dyestuff. Suitable dyestuffs in accordance with this invention are those which exhibit a sufficient affinity to proteins, which are directly absorbed and fast to oxidation and alkalis, and which do not contribute to agglutination of the microorganisms due to their lack of reactive groups. It is especially recommended to dye the microorganisms with dyestuffs of the Color Index (CI) denominations Basic Red 23, Basic Blue 45 or Basic Orange 30.

For the dyeing, the microorganims extracted according to this invention are suspended in an aqueous solution, a dilute solution of the corresponding dyestuff is added and, after a favorable residence time to be determined by tests, the microorganisms are separated from the dyestuff solution, which separation is advantageously carried out by high-speed centrifugation, for example at 10,000 to 20,000 $\times$ g. Suspended in one of the above buffers and with a suspension stabilizer added, the dyed microorganisms are especially suitable reagent components for the detection of fibrin fission products. Optionally, the dyed microorganisms may be stored in deep-frozen state and resuspended before use.

The dyeing of the microorganisms allows an especially clear reading of the reaction, since the dyed particles contribute considerably to increase the contrast to the environment. A further advantage resides in the possibility of decreasing the concentration of the microorganisms in the test system, which results in an increased sensitivity and a clearer reading of the termination points of the reaction.

Clumping Factor-positive microorganisms are known from the literature. Clumping Factor-positive microorganisms inactivated by means of heat are used for determining fibrin fission products. The process of the invention may be carried out using all these microorganisms strains known from the literature, and reagents with decreased tendency to disturbance can be prepared from these strains. Especially good results from the viewpoint of a decreased tendency to disturbances of the process for the detection of fibrinogen and fibrin fission products are obtained with the use of a *Staphylococcus aureus* denominated K 807 (ATCC No. 31243) the characteristics of which are described in the following manner:

The strain was isolated from a cow affected by mastitis. In a liquid nutrient its growth is diffuse. It is gram-positive. Further characteristic properties:

Crystal violet: type A
Clumping Factor: +
Coagulase: +
Protein A: +
Panton Valentine Leucocidin (PVL): −
PVL b (bovine): +
haemolysines α: +β: +δ: −
acid phosphatase: +
alkaline phosphatase: −
fibrinolysin: +
Yolk Factor: −
Penicillinase: −
Nuclease: +

Growth on solid media

Staphylococcus Medium 110 (Baltimore Biological Lab.): good growth, whitish-grey colonies having diameters of 1-2 mm Horse blood agar: good growth, whitish-grey colonies, scarcely haemolytic Nutritive agar: whitish-grey colonies, sometimes of irregular growth. Mac Concey agar No. 3 (oxoid): no growth.

| Antibiogram: | |
|---|---|
| Chloramphenicol | sensitive |
| Erythromycin | " |
| Sulphafurazole | resistant |
| Methicillin | sensitive |
| Penicillin | " |
| Ampicillin | " |
| Streptomycin | " |
| Tetracycline | " |

The *Staphylococcuss aureus* K 807 strain gives the following metabolic yields:

| Fermentation of: | | | |
|---|---|---|---|
| dextrose | after 6 days | at 37° C. | ++ |
| lactose | after 6 days | at 37° C. | ++ |
| saccharose | after 6 days | at 37° C. | ++ |
| maltose | after 6 days | at 37° C. | ++ |
| mannitol | after 6 days | at 37° C. | ++ |
| salicin | after 13 days | at 37° C. | − |
| inulin | after 13 days | at 37° C. | − |
| esculin | after 13 days | at 37° C. | − |
| Growth in the presence of NaCl: | | | |
| 4% | + | | |
| 5% | + | | |
| 6% | + | | |
| 7% | + | | |
| 8% | + | | |

Subject of the present invention is therefore especially a reagent for the detection of fibrinogen and/or fibrin fission products, which contains as active component a 0.1 to 10% suspension of homogeneously distributed Clumping Factor-positive microorganisms extracted in accordance with the invention, preferably a Clumping Factor-positive *Staphylococcus aureus*, especially the *Staphylococcus aureus* K 807 (ATCC No. 31243), optionally dyed with a suitable dyestuff.

Subject of this invention is furthermore the use of the cited microorganism suspension for the determination of fibrinogen and/or fibrin fission products in body fluids, preferably plasma or serum, according to known methods. After incubation of a portion each of the reagent suspension with a portion each of the solution to be determined in gradually increasing dilution state, the batches are advantageously shaken for a few minutes, and that highest dilution degree of the body fluid is recorded which still yields a positive clumping of the germs. When this value is put in relation to a value obtained by diluting the serum of sound persons, the result can be stated as deviation from the normal value.

For the determination of antigens in solution as well as on the surface of fine particles such as bacteria or viruses, microorganisms which are capable of binding the $F_c$ part of immune globulins are extracted in accordance with the process as described above. Via the antigen-binding parts of the immune globulins, an active linkage to the antigens to be determined is established. The agglutination of the microorganisms loaded with the immune globulin can be easily observed and recorded. An especially suitable microorganism having a $F_c$-binding polypeptide is, as already mentioned, *Staphylococcus aureus*. Furthermore, some strains of *Streptococcus pyogenes* may be cited as polypeptide carriers which can react with the $F_c$ part of immune globulins.

After extraction according to the invention, these microorganisms may be used for the diagnosis of physiological or pathological conditions both of man and animal where antigens are involved. For this purpose, a sample containing the antigen is contacted with specific antibodies bound to the surface of the microorganisms, whereupon an agglutination occurs in the case where the sample contains a corresponding antigen.

Guanidine chloride extracted, unencapsulated staphylococci (*Staphylococcus aureus* and *Staphylococcus epidermis*) activate the complementary factor C3 and adsorb it on their surface after incubation in fresh human and guinea pig serum. The staphylococci bearing activated C3 form rosettes with B-lymphocytes of humans; guanidine chloride extracted staphylococci thus allow the detection and isolation of B-lymphocytes. Alternatively, quanidine chloride extracted protein A-positive staphylococci may be used directly for this purpose.

The determination may be carried out quantitatively according to usual agglutination methods, for example by testing a dilution series of samples and comparing the result with samples of known antigen concentration. Generally, the agglutination test is carried out in an aqueous solution, for example a physiologically buffered saline solution having a neutral pH.

In a special embodiment of the invention, the extracted microorganisms capable of binding an $F_c$ part of antibodies may be dyed as described, in order to facilitate the observation of agglutinations.

Subject of the present invention is furthermore the agent in its most general form prepared in accordance with this invention, and especially a process for determining an antigen with the use of a microorganism extracted in accordance with this invention, according to known methods, for example agglutination, radio immunoassay or enzyme marked immunoassay.

The following example illustrates the invention.

EXAMPLE

*Staphylococcus aureus* K 807 (ATCC No. 31243) is grown in a medium of the following composition:

Preliminary culture: TSB (Tryptone Soya Broth, oxoid), 100 ml in 1.000 ml Erlenmeyer flasks Main culture: 14 liters of TSB in 16 liter fermentor with addition of 0.25% Liebig's extract (B.B.L.B.); inoculation with 6 flasks of preliminary culture.

The germs are obtained after centrifugation at 74,000×g, subsequently washed twice in distilled water, and deep-frozen. About 50 g of staphylococci are obtained from a 16 liter fermentor. The bacteria from one fermentor are allowed to stand for 18 hours after the addition of 200 ml of 6 M guanidine hydrochloride solution. Subsequently, the germs are separated from the guanidine hydrochloride solution, and the treatment with guanidine hydrochloride is repeated 4 times altogether. Finally, the staphylococci are washed or dialyzed with the use of alkaline, 1,2-naphthoquinone-4-sulfonic acid and hydroxyl amine according to Sullivan and Hess (Hoppe Seyler Thierfelder, Physiologie and Phathol. Chemische Analyse, 10 th ed., vol. III, 2, p. 1091, 1936) until guanidine hydrochloride can be detected only in traces. After resuspension of the staphylococci in distilled water, the germs are lyophilized. For dyeing, the lyophilized extracted germs are suspended in a concentration of 1.5 mg/ml in 0.14 M NaCl; 0.3 ml/ml of a 0.1% solution of Astrazonrot BBL ® (trade mark of Farbenfabriken Bayer AG, Leverkusen, Germany)=CI Basic Red 23 in 0.14 M saline solution is added, and the whole is stirred for 5 minutes. Subsequently, the styphylococci are centrifuged off at 14,600×g, and the germs are suspended in the original volume of 0.14 g phosphate buffered saline solution having a pH of 6.4. The buffer contains 0.05% of bovine serum albumin. For the Clumping Factor reaction in the vial test, the staphylococci are used in the form of a 1% suspension, for example in 0.05 M trishydroxymethyl-aminomethane buffer having a pH of 7.4, with addition of 0.01% bovine serum albumin.

For the micro-titration process according to Leavelle [Amer. J. Clin. Path., 55, 452-457 (1971)], the staphylococci are used in the form of a 0.3% suspension in a 0.017 M imidazole/NaCl buffer having a pH of 7.4. For mixing the reaction batch, a plate shaker (micro-shaker AM 69 of Flow Laboratories, Bonn, Germany) has proved to be especially advantageous.

For methods of antigen detection, the use of extracted protein A containing staphylococci, especially *Staphylococcus aureus* COWAN I (NCTT 8 530) strain, are advantageous, and extraction is carried out in the same manner as that of K 807.

What is claimed is:

1. A method for eliminating undesirable portions of a Staphylococcus microorganism selected from the group consisting of Clumping Factor-positive Staphylococcus microorganisms and Staphylococcus microorganisms containing $F_c$-reactive protein A and capable of entering into a binding reaction with the $F_c$ part of an antibody molecule, which method comprises extracting such a microorganism with a 4 to 8 molar solution of a guanidine salt under conditions sufficient to remove coagulase, non-characterized proteins tending to cause agglutination, and other interfering proteins from said microorganism, subsequently washing said microorganism to remove the guanidine salt therefrom, and recovering a Clumping Factor-positive Staphylococcus microorganism which is free of proteins interfering with use of the microorganism as a diagnostic agent for the detection of fibrinogen or fibrin fission products or recovering a Staphylococcus microorganism containing $F_c$-reactive protein A which is free of proteins interfering with use of the microorganism, when bound to the $F_c$-part of immune globulin, as a diagnostic for determining antigens.

2. A method as in claim 1 wherein said microorganism is *Staphylococcus aureus* K 807 (ATCC 31243).

3. A method as in claim 1 wherein said microorganism is *Staphylococcus aureus* Cowan I.

4. An extracted Clumping Factor-positive microorganism free of coagulase, non-characterized proteins tending to cause agglutination, and other proteins interfering with use of the microorganism as a diagnostic agent for the detection of fibrinogen or fibrin fission products, prepared by the method of claim 1.

5. An agent for detecting fibrinogen and fibrin fission products, which agent comprises an extracted microorganism as in claim 4 suspended in a carrier.

6. An agent as in claim 3 wherein said extracted microorganism is dyed with a dyestuff.

7. An agent as in claim 6 wherein said dyestuff is Color Index Basic Red 23.

8. An agent as in claim 3 wherein said extracted microorganism is *Staphylococcus aureus* K 807 dyed with Color Index Basic Red 23.

9. An agent as in claim 3 wherein said carrier is an aqueous buffer solution comprising from 3 to 50 percent of a water-soluble polyol as a stabilizer.

10. An extracted microorganism containing $F_c$-reactive protein A free of coagulase, non-characterized proteins tending to cause agglutination, and other proteins interfering with use of the microorganism, when bound to the $F_c$-part of immune globulin, as a diagnostic for determining antigens, prepared by the method of claim 1.

11. An agent for determining an antigen, which agent comprises an extracted microorganism as in claim 10 bound to an antibody and suspended in a carrier.

12. An agent as in claim 11 wherein said carrier is an aqueous buffer solution comprising from 3 to 50 percent of a water-soluble polyol as a stabilizer.

13. An agent for detecting and isolating B-lymphocytes, which agent comprises an extracted microorganism as in claim 10 suspended in a carrier.

14. An agent as in claim 13 wherein said carrier is an aqueous buffer solution comprising from 3 to 50 percent of a water-soluble polyol as a stabilizer.

15. An extracted clumping Factor-positive *Staphylococcus aureus* K 807 (ATCC 31243) free of coagulase, non-characterized proteins tending to cause agglutination, and other proteins interfering with use of the microorganism as a diagnostic agent for the detection of fibrinogen or fibrin fission products.

* * * * *